United States Patent

Canzek

[11] Patent Number: 5,461,509
[45] Date of Patent: Oct. 24, 1995

[54] MODULAR OPTICAL RELAY LENS SYSTEM

[75] Inventor: Ludvik Canzek, Unterentfelden, Switzerland

[73] Assignee: Canzek Endoskopie A.G., Unterentfelden, Switzerland

[21] Appl. No.: 101,150

[22] Filed: Aug. 2, 1993

[30] Foreign Application Priority Data

Aug. 22, 1992 [CH] Switzerland ............ 02601/92

[51] Int. Cl.$^6$ ..................... G02B 9/34
[52] U.S. Cl. ............ 359/435; 359/362; 359/434
[58] Field of Search ............ 359/362, 423–429, 359/434–435, 722, 754, 795–797

[56] References Cited

U.S. PATENT DOCUMENTS

| | | | |
|---|---|---|---|
| 4,575,195 | 3/1986 | Hoogland | 359/435 |
| 4,946,267 | 8/1990 | Hoogland | 359/435 |
| 5,005,960 | 4/1991 | Heimbeck | 359/435 |
| 5,142,410 | 8/1992 | Ono et al. | 359/435 |

FOREIGN PATENT DOCUMENTS 2619393 11/1976 Germany.
3534210 3/1986 Germany.

OTHER PUBLICATIONS

"Modern Optical Engineering", McGraw Hill Book Company Warren J. Smith, pp. 212–213.

Primary Examiner—Paul M. Dzierzynski
Assistant Examiner—Thong Nguyen
Attorney, Agent, or Firm—Cohen, Pontani, Lieberman & Pavane; Christa Hildebrand

[57] ABSTRACT

The present invention relates to a relay lens system, wherein all image aberrations are corrected. This permits modular use with no stand-alone lenses or lenses with great focal distance. The relay lens system comprises at least two subsystems, wherein at least one positive lens and at least one negative lens are placed in at least one subsystem near the intermediate image, and the refractive index N(+) of at least one positive lens and the refractive index N(−) of at least one negative lens and the total focal distance F(FLD) of the lenses of the subsystem near the intermediate image correspond to the following relations:

$N(+) > N(-)$ and $F(FLD) > 0$.

3 Claims, 1 Drawing Sheet

MODULAR OPTICAL RELAY LENS SYSTEM

FIELD OF THE INVENTION

The present invention relates to an optical relay lens system, comprising at least two subsystems.

BACKGROUND OF THE INVENTION

Optical relay systems of this kind are used e.g. in endoscopes or similar optical devices. A relay system images the object F1, generated by an objective lens into the image F2. Endoscopes comprise also several relay systems, mounted one after the other and generating a last intermediate image in the focal plane of the ocular lens or, with or without an additional lens, on a detector, e.g. film or CCD.

Relay systems of this kind are known. FIG. 1 shows a simple example, wherein all image aberrations may be corrected. However, this system has a very pronounced vignetting making it almost unusable for film and television applications. Another known system, shown in FIG. 2, allows to eliminate the vignetting but does not allow to correct the image field. The aberrations multiply with the number of relay systems mounted in the optical device. This problem is solved in the state of the art with compensating objective and/or ocular lenses. With such lenses, however, a different objective or ocular must be used each time, the number of relay systems is changed in order to vary the overall length or the image orientation. A further disadvantage lies in the fact that the uncorrected separations demand narrow tolerances and that the possibility of compensating such an objective lens implies a given limit for the number of relay systems.

Further, relay systems are known, e.g. according to German DE 2,619,393-C2 or German DE 3,534,210-A1, wherein the image field may be corrected and the vignetting may be eliminated. A disadvantage of these systems is, however, that they comprise uncemented lenses with large focal distances which are difficult to center and consequently of elevated cost. They also require a very precise mounting.

The principal object of the present invention is to design a relay lens system, wherein all image aberrations may be corrected, which therefore permits modular use, and which has no stand-alone lenses or lenses with great focal distance.

SUMMARY OF THE INVENTION

This object is solved with a relay lens system comprising at least two subsystems, wherein at least one positive lens and at least one negative lens are placed in at least one subsystem near the intermediate image, and the refractive index $N(+)$ of at least one positive lens and the refractive index $N(-)$ of at least one negative lens and the total focal distance $F(FLD)$ of the lenses of the subsystem near the intermediate image correspond to the following relations:

$N(+)>N(-)$ and $F(FLD)>0$.

BRIEF DESCRIPTION OF THE DRAWINGS

The invention will be understood better with the description of the preferred embodiments below, given by way of nonlimiting examples, and explained with reference to the accompanying diagrammatic figures, in which.

DETAILED DESCRIPTION

All of the embodiments of the systems shown have a symmetric design and great part of the lenses are cemented. In the tables below, data for symmetrically designed relay systems are given. For reasons of symmetry data are given for one symmetric component only.

Figure 3:
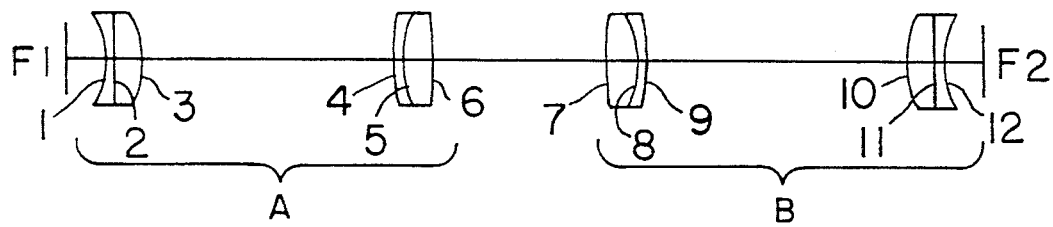
FIG. 3 is a diagrammatic representation of a relay system according to the invention having no rod lenses.

FIG. 3 shows the example according to table 1.

TABLE 1

| Surface Number | Radius | Distance | Refractive Index | Abbe-number |
|---|---|---|---|---|
| 1 | −6.39 | 0.6 | 1.53 | 49 |
| 2 | −83.70 | 1.0 | 1.79 | 50 |
| 3 | −6.89 | 19.5 | 1 | |
| 4 | 17.18 | 0.6 | 1.71 | 30 |
| 5 | 7.30 | 1.0 | 1.59 | 51 |
| 6 | −37.01 | 12.3 | 1 | |
| 7 | 37.01 | 1.0 | 1.59 | 51 |
| 8 | −7.3 | 0.6 | 1.71 | 30 |
| 9 | −17.18 | 19.5 | 1 | |
| 10 | 6.89 | 1.0 | 1.79 | 50 |
| 11 | 83.70 | 0.6 | 1.53 | 49 |
| 12 | 6.39 | | 1 | |

In this example:

$N(+)=1.79>N(-)=1.53$ and $F(FLD)=26.485>0$

Figure 4:
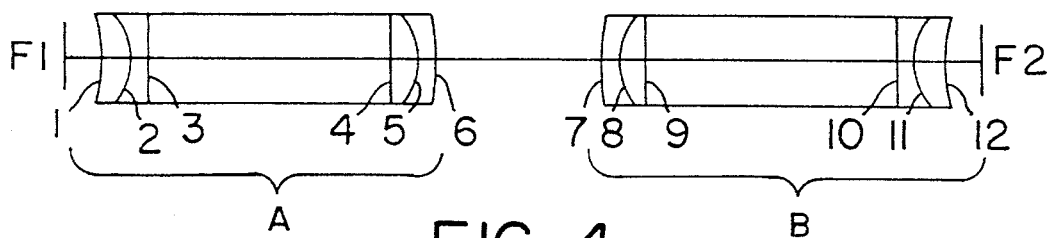
FIG. 4 represents a simple relay system according to the invention having rod lenses.

FIG. 4 shows the example according to table 2.

TABLE 2

| Surface Number | Radius | Distance | Refractive Index | Abbe-number |
|---|---|---|---|---|
| 1 | −22.8 | 1.0 | 1.82 | 44 |
| 2 | −4.1 | 0.6 | 1.47 | 66 |
| 3 | ∞ | 24.0 | 1.58 | 41 |
| 4 | ∞ | 0.8 | 1.59 | 49 |
| 5 | −5.7 | 0.6 | 1.74 | 28 |
| 6 | −9.7 | 4.9 | 1 | |
| 7 | 9.7 | 0.6 | 1.74 | 28 |
| 8 | 5.7 | 0.8 | 1.59 | 49 |
| 9 | ∞ | 24.0 | 1.58 | 41 |
| 10 | ∞ | 0.6 | 1.47 | 66 |
| 11 | 4.1 | 1.0 | 1.82 | 44 |
| 12 | 22.8 | | 1 | |

In this example:

$N(+)=1.82>N(-)=1.47$ and $F(FLD)=19.574>0$

Figure 5:
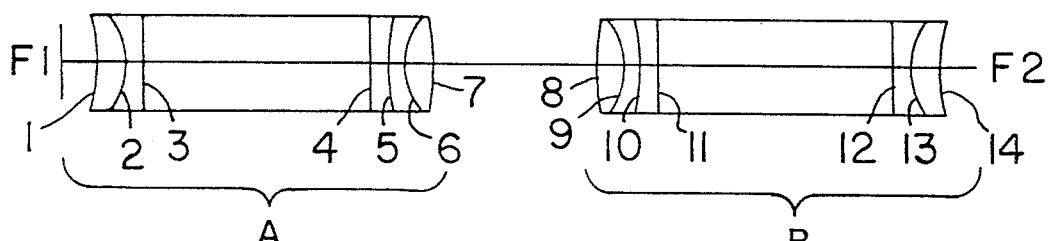
FIG. 5 shows a diagram of another relay system according to the invention and having rod lenses.

FIG. 5 shows the example according to table 3.

TABLE 3

| Surface Number | Radius | Distance | Refractive Index | Abbe-number |
|---|---|---|---|---|
| 1 | −32.1 | 0.9 | 1.81 | 25 |
| 2 | −3.6 | 0.7 | 1.57 | 56 |
| 3 | ∞ | 19.5 | 1.55 | 64 |
| 4 | ∞ | 0.6 | 1.53 | 65 |
| 5 | 9.9 | 0.6 | 1.85 | 32 |
| 6 | 3.0 | 1.0 | 1.835 | 43 |

TABLE 3-continued

| Surface Number | Radius | Distance | Refractive Index | Abbe-number |
|---|---|---|---|---|
| 7 | −27.3 | 11.2 | 1 | |
| 8 | 27.3 | 1.0 | 1.835 | 43 |
| 9 | −3.0 | 0.6 | 1.85 | 32 |
| 10 | −9.9 | 0.6 | 1.53 | 65 |
| 11 | ∞ | 19.5 | 1.55 | 64 |
| 12 | ∞ | 0.7 | 1.57 | 56 |
| 13 | 3.6 | 0.9 | 1.81 | 25 |
| 14 | 32.1 | | 1 | |

In this example:

$$N(+)=1.81>N(-)=1.57 \text{ and } F(FLD)=23.658>0$$

Figure 1:
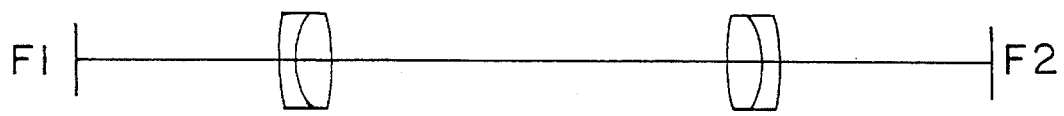
FIG. 1 represents a relay system according to the state of the art.
Figure 2:
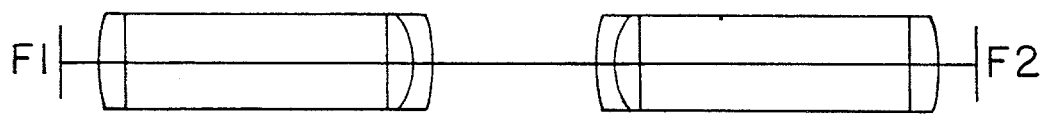
FIG. 2 represents another relay system according to the state of the art.

The subsystems of the relay systems according to the invention and having various relay lengths may be combined with each other or with subsystems of known relay systems in such a way, that their effect is magnifying, reducing or only image relaying. A subsystem, e.g. according to FIG. 3 or FIG. 4, may be combined with a subsystem according to one of FIGS. 1, 2 or 5.

Optical calculations have shown that systems according to the invention may be corrected very well, and that they may be used as modular relay systems. These systems have no uncemented lenses with large focal distances, and the vignetting may be eliminated to a high degree. If relay systems according to the invention are manufactured as symmetric systems with cemented lenses, the design is very simple and production will be of low cost.

Although particular preferred embodiments of the invention have been disclosed in detail for illustrative purposes, it will be recognized that variations or modifications of the disclosed apparatus, including the rearrangement of parts, lie within the scope of the present invention.

I claim:

1. An optical relay lens system comprising subsystems A, B, wherein at least one positive lens and at least one negative lens are placed in at least one subsystem A or B near an object F1 or an image F2, the refractive index N(+) of at least one positive lens and the refractive index N(−) of at least one negative lens and the total focal distance F(FLD) of the subsystem A or B near the object F1 or the image F2 correspond to the following relations:

$$N(+)>N(-) \text{ and } F(FLD)>0,$$

and having following numerical values:

| Surface Number | Radius | Distance | Refractive Index | Abbe-number |
|---|---|---|---|---|
| 1 | −6.39 | 0.6 | 1.53 | 49 |
| 2 | −83.70 | 1.0 | 1.79 | 50 |
| 3 | −6.89 | 19.5 | 1 | |
| 4 | 17.18 | 0.6 | 1.71 | 30 |
| 5 | 7.30 | 1.0 | 1.59 | 51 |
| 6 | −37.01 | 12.3 | 1 | |
| 7 | 37.01 | 1.0 | 1.59 | 51 |
| 8 | −7.3 | 0.6 | 1.71 | 30 |
| 9 | −17.18 | 19.5 | 1 | |
| 10 | 6.89 | 1.0 | 1.79 | 50 |
| 11 | 83.70 | 0.6 | 1.53 | 49 |
| 12 | 6.39 | | 1. | |

2. An optical relay lens system comprising subsystems A, B, wherein at least one positive lens and at least one negative lens are placed in at least one subsystem A or B near an object F1 or an image F2, the refractive index N(+) of at least one positive lens and the refractive index N(−) of at least one negative lens and the total focal distance F(FLD) of the subsystem A or B near the object F1 or the image F2 correspond to the following relations:

$$N(+)>N(-) \text{ and } F(FLD)>0,$$

and having following numerical values:

| Surface Number | Radius | Distance | Refractive Index | Abbe-number |
|---|---|---|---|---|
| 1 | −22.8 | 1.0 | 1.82 | 44 |
| 2 | −4.1 | 0.6 | 1.47 | 66 |
| 3 | ∞ | 24.0 | 1.58 | 41 |
| 4 | ∞ | 0.8 | 1.59 | 49 |
| 5 | −5.7 | 0.6 | 1.74 | 28 |
| 6 | −9.7 | 4.9 | 1 | |
| 7 | 9.7 | 0.6 | 1.74 | 28 |
| 8 | 5.7 | 0.8 | 1.59 | 49 |
| 9 | ∞ | 24.0 | 1.58 | 41 |
| 10 | ∞ | 0.6 | 1.47 | 66 |
| 11 | 4.1 | 1.0 | 1.82 | 44 |
| 12 | 22.8 | | 1 | |

3. An optical relay lens system comprising subsystems A, B, wherein at least one positive lens and at least one negative lens are placed in at least one subsystem A or B near an object F1 or an image F2, the refractive index N(+) of at least one positive lens and the refractive index N(−) of at least one negative lens and the total focal distance F(FLD) of the subsystem A or B near the object F1 or the image F2 correspond to the following relations:

$$N(+)>N(-) \text{ and } F(FLD)>0,$$

and having following numerical values:

| Surface Number | Radius | Distance | Refractive Index | Abbe-number |
|---|---|---|---|---|
| 1 | −32.1 | 0.9 | 1.81 | 25 |
| 2 | −3.6 | 0.7 | 1.57 | 56 |
| 3 | ∞ | 19.5 | 1.55 | 64 |
| 4 | ∞ | 0.6 | 1.53 | 65 |
| 5 | 9.9 | 0.6 | 1.85 | 32 |
| 6 | 3.0 | 1.0 | 1.835 | 43 |
| 7 | −27.3 | 11.2 | 1 | |
| 8 | 27.3 | 1.0 | 1.835 | 43 |
| 9 | −3.0 | 0.6 | 1.85 | 32 |
| 10 | −9.9 | 0.6 | 1.53 | 65 |
| 11 | ∞ | 19.5 | 1.55 | 64 |
| 12 | ∞ | 0.7 | 1.57 | 56 |
| 13 | 3.6 | 0.9 | 1.81 | 25 |
| 14 | 32.1 | | 1 | |

* * * * *